US00PP11795P2

(12) United States Plant Patent
VandenBerg

(10) Patent No.: US PP11,795 P2
(45) Date of Patent: Mar. 6, 2001

(54) CHRYSANTHEMUM PLANT NAMED 'YONASHVILLE'

(75) Inventor: Cornelis P. VandenBerg, Salinas, CA (US)

(73) Assignee: Yoder Brothers, Inc., Barberton, OH (US)

( * ) Notice: Under 35 U.S.C. 154(b), the term of this patent shall be extended for 0 days.

(21) Appl. No.: 09/275,120

(22) Filed: Mar. 24, 1999

(51) Int. Cl.[7] ..... A01H 5/00

(52) U.S. Cl. ..... Plt./286

(58) Field of Search ..... Plt./286, 297

(56) References Cited

U.S. PATENT DOCUMENTS

P.P. 9,105 * 4/1995 VandenBerg ..... Plt./286

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yonashville', characterized by its upright, outwardly spreading and uniformly mounded plant habit; large plant size; good vigor; freely branching habit; uniform and early flowering; numerous daisy-type inflorescences that are about 7.3 cm in diameter; purple-colored ray florets with bright yellow-colored disc florets; and excellent postproduction longevity with inflorescences and leaves maintaining good substance and color for about four or five weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yonashville.

The new Chrysanthemum is a product of a planned breeding program conducted by the Inventor in Salinas, Calif. The objective of the breeding program is to create new pot-type Chrysanthemum cultivars having desirable inflorescence forms and floret colors and good post-production longevity.

The new Chrysanthemum originated from a cross made by the Inventor in October, 1994, in Salinas, Calif., of the *Dendranthema grandiflora* cultivar Monterey, disclosed in U.S. Plant Pat. No. 7,753, as the female, or seed, parent, with the *Dendranthema grandiflora* cultivar Lucido, disclosed in U.S. Plant Pat. No. 6,586, as the male, or pollen, parent.

The new Chrysanthemum was discovered and selected by the Inventor as a flowering plant within the progeny of the stated cross in a controlled environment in Fort Myers, Fla., in November, 1995. The selection of this plant was based on its desirable inflorescence form and floret colors and good post-production longevity.

Asexual production of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Yonashville has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yonashville'. These characteristics in combination distinguish 'Yonashville' as a new and distinct Chrysanthemum:

1. Upright, outwardly spreading and uniformly mounded plant habit.

2. Large vigorous plants.

3. Freely branching habit, full and dense plants.

4. Uniform and early flowering.

5. Floriferous, numerous daisy-type inflorescences that are about 7.3 cm in diameter.

6. Purple-colored ray florets with bright yellow-colored disc florets.

7. Excellent postproduction longevity with inflorescences and leaves maintaining good substance and color for about four or five weeks in an interior environment.

The new Chrysanthemum can be compared to the Chrysanthemum cultivar Regal Davis, disclosed in U.S. Plant Pat. No. 8,292. However in side-by-side comparisons in Salinas, Calif., and Leamington, Ontario, Canada, under commercial practice, plants of the new Chrysanthemum differ from plants of the cultivar Regal Davis in the following characteristics:

1. Plants of the new Chrysanthemum are more vigorous and taller than plants of the variety Regal Davis.

2. Leaves of plants of the new Chrysanthemum are larger, darker green in color, and less susceptible to foliar problems than leaves of plants of the variety Regal Davis.

3. Plants of the new Chrysanthemum flower about one week earlier than plants of the cultivar Regal Davis.

4. Plants of the new Chrysanthemum have larger inflorescences than plants of the variety Regal Davis.

5. Plants of the new Chrysanthemum have a more open spray formation than plants of the variety Regal Davis.

6. Ray florets of the new Chrysanthemum are larger, flatter and slightly darker in color than ray florets of the cultivar Regal Davis.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Yonashville'.

The photograph at the bottom of the first sheet comprises a close-up view of upper (left) and lower (right) surfaces of typical inflorescences and upper (left) and lower (right) surfaces of typical leaves of the cultivar Yonashville.

The photograph at the top of the second sheet comprises a side perspective view of typical flowering plants of 'Yonashville' (left) and 'Regal Davis' (right).

The photograph at the bottom of the second sheet comprises a close-up view of upper surfaces of typical inflorescences and leaves of plants of 'Yonashville' (left) and 'Regal Davis' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Plants used for this description were grown as spray-types. Measurements and numerical values represent averages of typical flowering plants.

Botanical classification: *Dendranthema grandiflora* cultivar Yonashville.

Commercial classification: Daisy spray-type pot Chrysanthemum.

Parentage:

*Female or seed parent.*—*Dendranthema grandiflora* cultivar Monterey, disclosed in U.S. Plant Pat. No. 7,753.

*Male or pollen parent.*—*Dendranthema grandiflora* cultivar Lucido, disclosed in U.S. Plant Pat. No. 6,586.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy pot Chrysanthemum typically grown as a spray-type. Inverted triangle; large and vigorous with stems upright and outwardly spreading giving a uniformly mounded appearance to the plant. Freely branching; about four lateral branches develop after removal of terminal apex (pinching); dense and full plants.

*Plant height.*—About 35 cm.

*Plant width.*—About 52 cm.

*Stem color.*—Greener than 147A.

*Stem texture.*—Pubescent.

*Foliage description.*—Arrangement: Alternate. Length: About 8.4 cm. Width: About 4.8 cm. Apex: Cuspidate to mucronate. Base: Attenuate. Margin: Palmately lobed, sinuses between lateral lobes mostly parallel. Texture: Upper and lower surfaces with very fine pubescence; veins prominent on lower surface. Petiole length: About 1.8 cm. Color: Young foliage upper surface: Darker than 147A. Young foliage lower surface: Close to 147B. Mature foliage upper surface: 147A. Mature foliage lower surface: 147B. Venation upper surface: Close to 147B. Venation lower surface: 147B.

Inflorescence description:

*Appearance.*—Daisy inflorescence form with oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 7.5 to 8 weeks later.

*Postproduction longevity.*—Inflorescences and leaves will maintain good color and substance for about four or five weeks in an interior environment.

*Quantity of inflorescences.*—Very floriferous; about 11 inflorescences per lateral branch or about 44 inflorescences per plant.

*Inflorescence bud.*—Height: About 5 mm. Diameter: About 8 mm. Color: 147A.

*Inflorescence size.*—Diameter: About 7.3 cm. Depth (height): About 1.2 cm. Diameter of disc: About 1.6 cm.

*Ray florets.*—Shape: Oblong with short corolla tube. Orientation: Slightly upright. Aspect: Straight, mostly flat. Length: About 3.4 cm. Width: About 1 cm. Apex: Acute. Margin: Entire. Texture: Smooth, glabrous. Number of ray florets per inflorescence: About 26. Color: When opening: Purple, 78B. Fully opened, upper surface: Purple, 77B–78B. Fully opened, lower surface: Light purple, 77D.

*Disc florets.*—Shape: Tubular. Apex: Serrated. Length: About 6 mm. Width: Apex: About 1.5 mm. Base: About 1 mm. Number of disc florets per inflorescence: Numerous, about 178. Color: Immature: Greener than 154A. Mature: Apex: 9A. Mid-section: Light green. Base: White, 155D.

*Peduncles.*—Aspect: Angled about 50° to stem. Strength: Strong, but flexible. Length: First peduncle: About 5.7 cm. Fourth peduncle: About 8.1 cm. Texture: Pubescent. Color: Greener than 147A.

*Reproductive organs.*—Androecium: Present on disc florets only. Anther color: 13A. Pollen: Amount: Scarce. Color: 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yonashville', as illustrated and described.

* * * * *

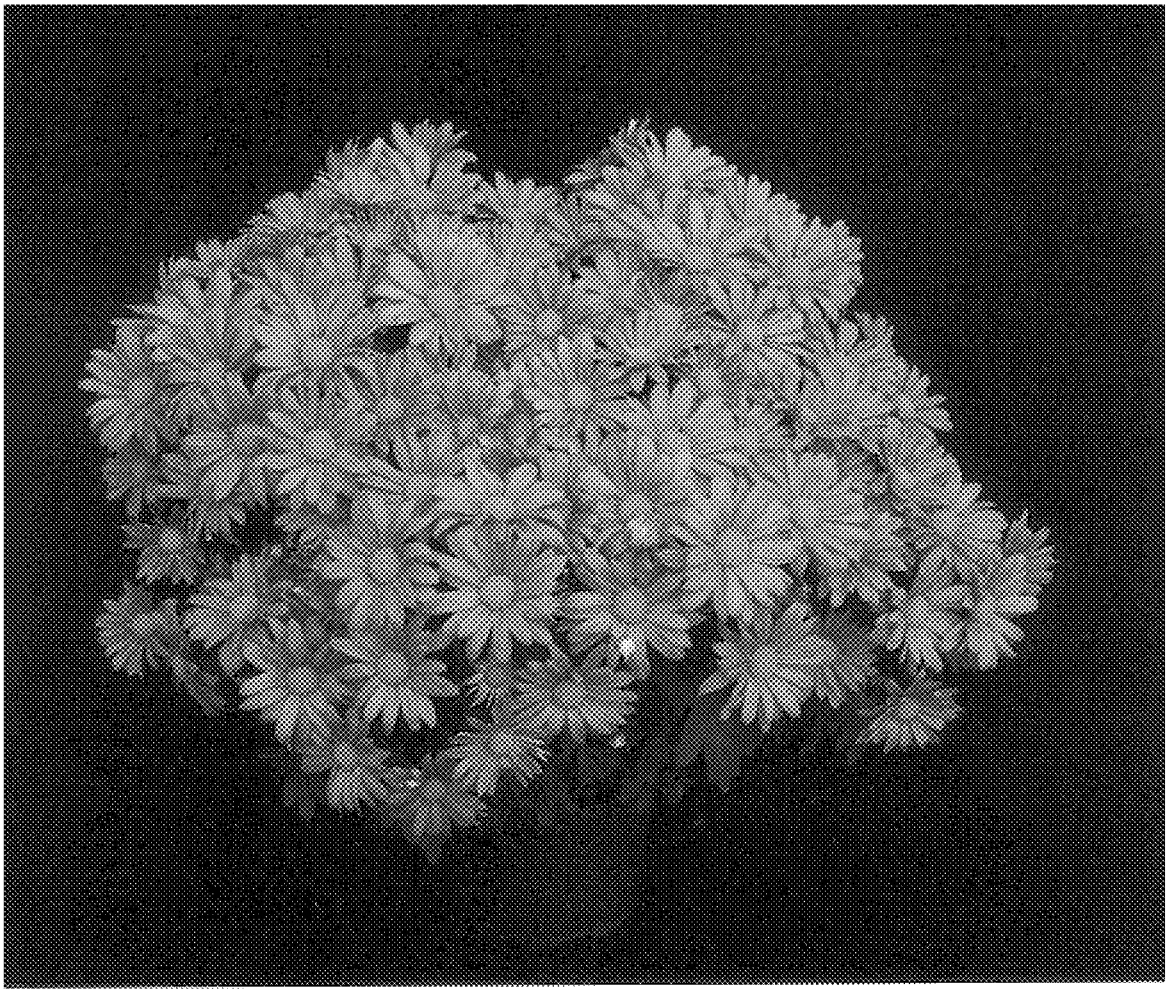
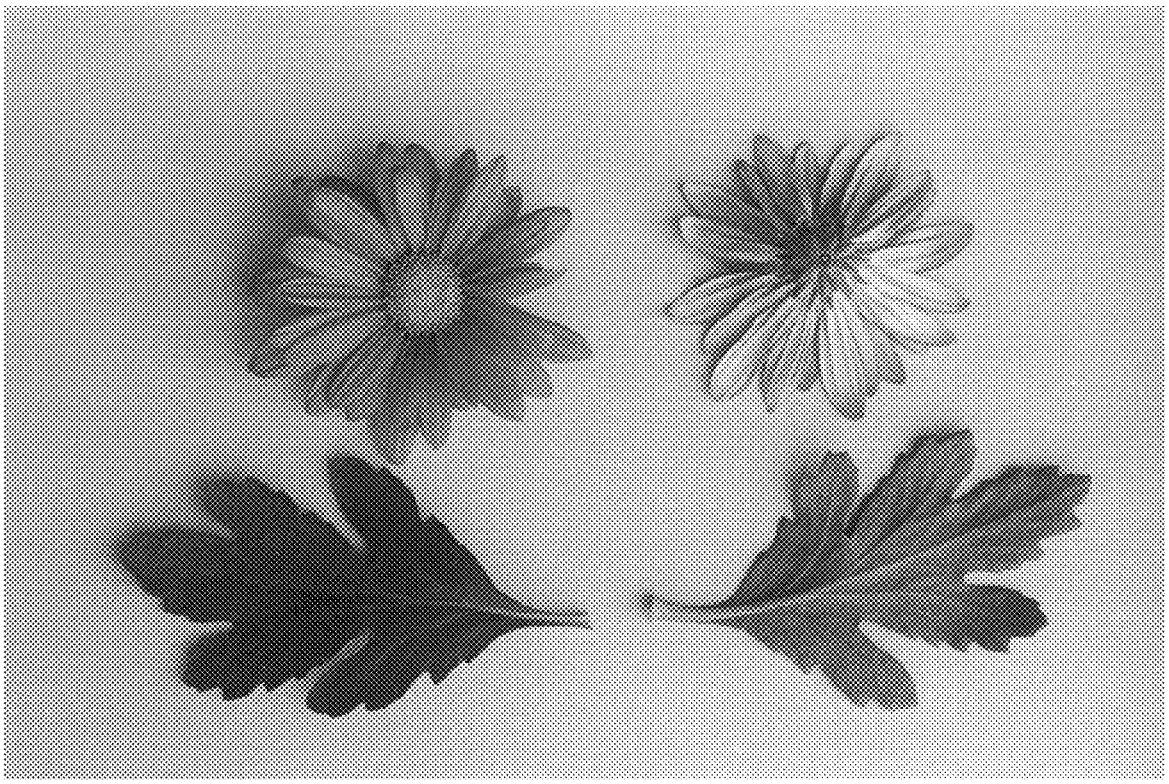

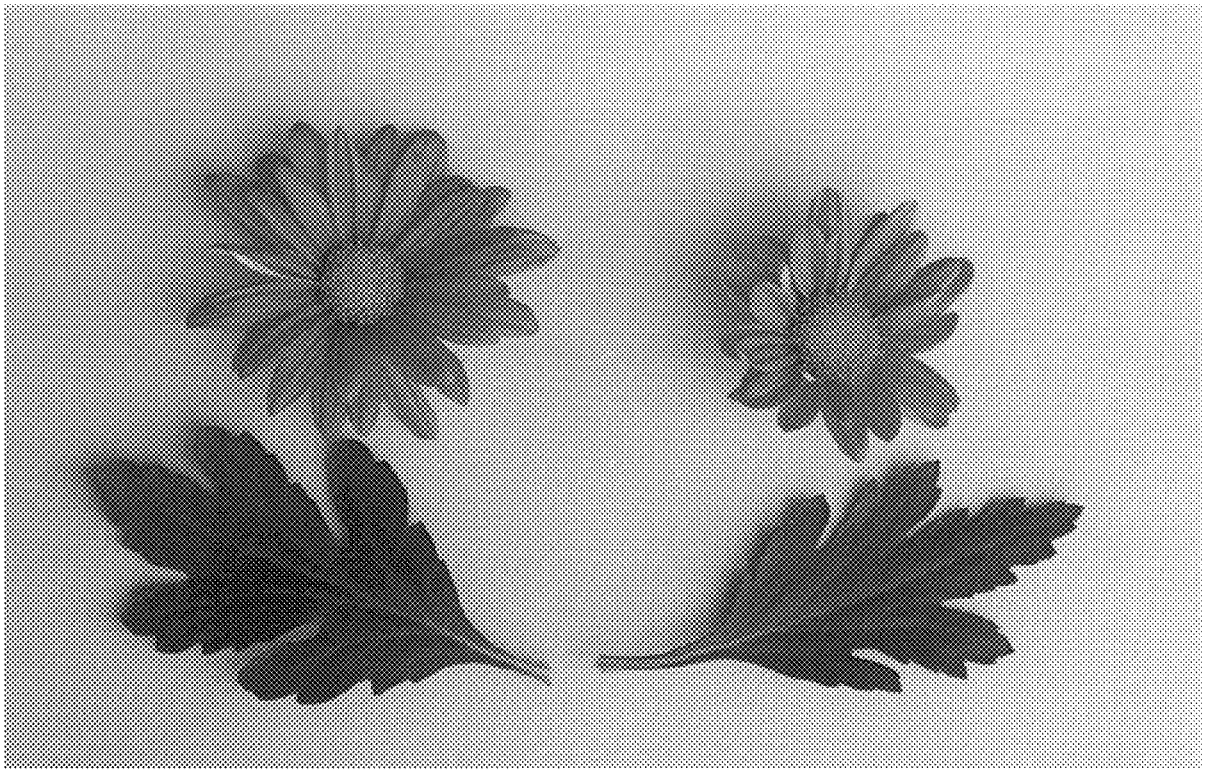

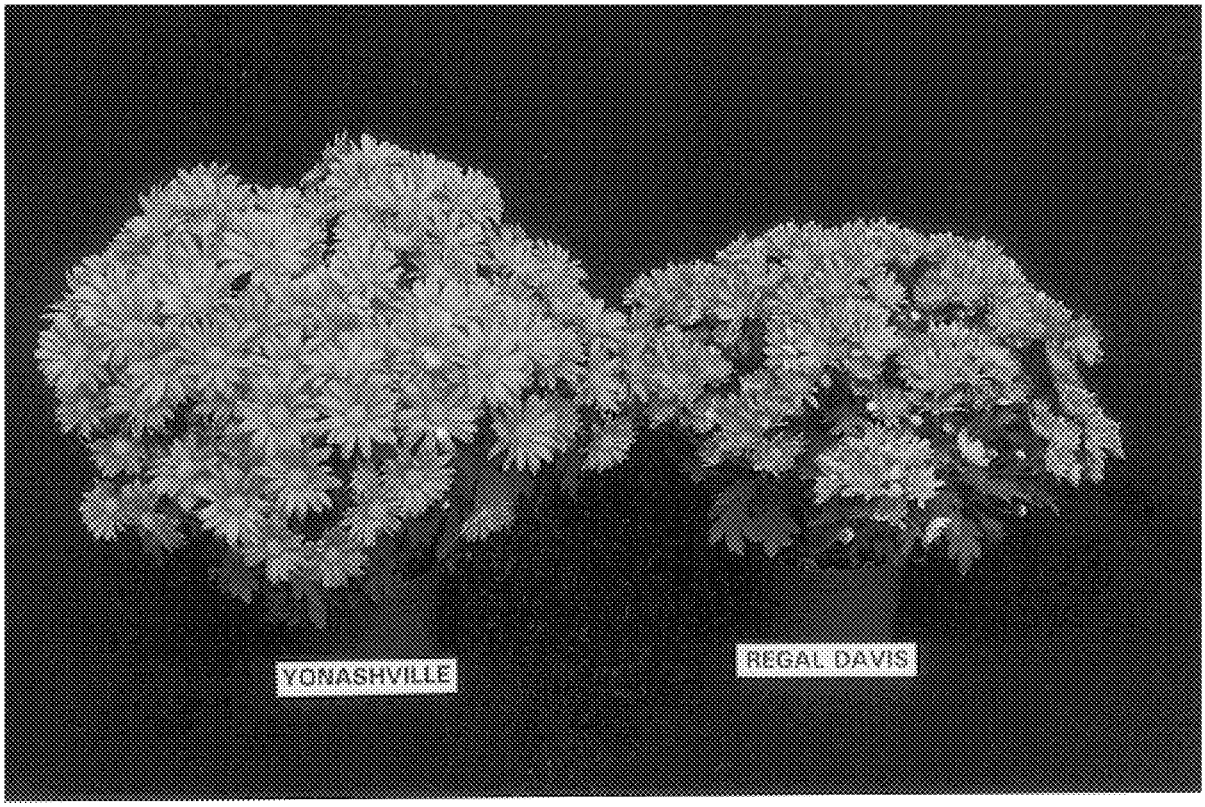
YONASHVILLE
REGAL DAVIS